(12) United States Patent
Friedli

(10) Patent No.: US 11,771,827 B2
(45) Date of Patent: Oct. 3, 2023

(54) MEDICAL DEVICE AND METHOD OF OPERATING A MEDICAL DEVICE AND DETECTION OF A SHORT CIRCUIT

(71) Applicant: Roche Diabetes Care, Inc., Indianapolis, IN (US)

(72) Inventor: Kurt Friedli, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 116 days.

(21) Appl. No.: 16/792,595

(22) Filed: Feb. 17, 2020

(65) Prior Publication Data
US 2020/0179604 A1 Jun. 11, 2020

Related U.S. Application Data

(63) Continuation of application No. PCT/EP2018/072109, filed on Aug. 15, 2018.

(30) Foreign Application Priority Data

Aug. 18, 2017 (EP) .................................... 17186814

(51) Int. Cl.
*A61M 5/00* (2006.01)
*A61M 5/172* (2006.01)
(Continued)

(52) U.S. Cl.
CPC ......... *A61M 5/1723* (2013.01); *G06F 3/0482* (2013.01); *G06F 11/221* (2013.01);
(Continued)

(58) Field of Classification Search
CPC ...... A61M 2205/18; A61M 2205/3317; A61M 2205/502; A61M 5/172; A61M 5/5086;
(Continued)

(56) References Cited

U.S. PATENT DOCUMENTS 4,698,582 A * 10/1987 Braun et al. ............ G05F 1/573
323/285
6,075,296 A * 6/2000 Kasbergen ............ G06F 11/221
307/139
(Continued)

FOREIGN PATENT DOCUMENTS

CN 2117169 U 9/1992
CN 2369694 Y 3/2000
(Continued)

OTHER PUBLICATIONS

International Search Report and Written Opinion of the International Searching Authority, PCT/EP2018/072109, dated Nov. 14, 2018, 9 pages.
(Continued)

*Primary Examiner* — Katherine H Schwiker
*Assistant Examiner* — Anna E Goldberg-Richmeier
(74) *Attorney, Agent, or Firm* — Bose McKinney & Evans LLP

(57) ABSTRACT

This disclosure concerns a medical device designed for delivering a medical fluid or designed for controlling delivery of a medical fluid, and to a method of operating such a medical device. The medical device comprises a user interface associated with an electronic circuit connected to a first port and to a second port of a controller. The electronic circuit enables the controller to detect actuation of the user interface. The controller is configured to execute the following sequence of steps: first step: configure the first port as an output port and to apply a first signal to the first port; second step: to acquire a second signal from the second port; and third step: to determine on the basis of the second signal if a short circuit has occurred and to generate a short circuit alert signal if applicable.

15 Claims, 3 Drawing Sheets

(51) Int. Cl.
*G06F 3/0482* (2013.01)
*G06F 11/22* (2006.01)

(52) U.S. Cl.
CPC . *A61M 2205/18* (2013.01); *A61M 2205/3317* (2013.01); *A61M 2205/502* (2013.01); *A61M 2205/505* (2013.01); *A61M 2230/201* (2013.01); *G06F 11/2205* (2013.01); *G06F 11/2215* (2013.01); *G06F 11/2221* (2013.01)

(58) Field of Classification Search
CPC ........ A61M 5/142; A61M 2005/14208; A61M 5/14244; A61M 5/14248; A61M 2005/142; A61M 5/1723; A61M 2005/1726; A61M 2005/3125; A61M 5/3126; A61M 2205/50; G06F 11/22; G06F 11/2205; G06F 11/221; G06F 11/2215; G06F 11/2221
See application file for complete search history.

(56) References Cited

U.S. PATENT DOCUMENTS

| | | | |
|---|---|---|---|
| 2002/0040208 | A1 | 4/2002 | Flaherty et al. |
| 2009/0254025 | A1* | 10/2009 | Simmons .......... A61M 2205/18 604/67 |
| 2011/0004186 | A1 | 1/2011 | Butterfield |
| 2012/0253262 | A1 | 10/2012 | Lemke et al. |
| 2016/0000998 | A1 | 1/2016 | Estes |

FOREIGN PATENT DOCUMENTS

| | | | | |
|---|---|---|---|---|
| CN | 2512442 | Y | 9/2002 | |
| IL | WO 2009013736 | A1 * | 1/2009 | ........ A61M 5/14248 |
| JP | H02-13456 | A | 1/1990 | |
| JP | 2010-534085 | A | 11/2010 | |
| JP | 2014-516281 | A | 7/2014 | |
| RU | 93 146 | U1 | 4/2010 | |
| RU | 2 547 074 | C2 | 4/2015 | |
| WO | WO 2004/093648 | A2 | 11/2004 | |
| WO | WO 2009/013736 | A1 | 1/2009 | |
| WO | WO 2012/134766 | A2 | 10/2012 | |
| WO | WO 2016/040423 | A1 | 3/2016 | |

OTHER PUBLICATIONS

International Preliminary Reporton Patentability, PCT/EP2018/072109, dated Jan. 7, 2020, 5 pages.

\* cited by examiner

MEDICAL DEVICE AND METHOD OF OPERATING A MEDICAL DEVICE AND DETECTION OF A SHORT CIRCUIT

RELATED APPLICATIONS

This application is a continuation of PCT/EP2018/072109, filed Aug. 15, 2018, which claims priority to EP 17 186 814.4, filed Aug. 18, 2017, both of which are incorporated herein by reference in their entirety.

BACKGROUND

This disclosure relates to a medical device designed for delivering a medical fluid or designed for controlling delivery of a medical fluid. This disclosure further relates to a method of operating a medical device designed for delivering a medical fluid or designed for controlling delivery of a medical fluid. This disclosure relates to the detection of a short circuit in the medical device.

In the state of the art, widely used are medical devices designed for controlling delivery of a medical fluid, such as insulin pumps for delivering an amount of insulin, glucose meters for determining the glucose level, remote controls for controlling a medical device for delivering a medical fluid, etc. These medical devices include user interfaces enabling patients or health personnel to control the medical device. For example, a diabetes patient may actuate elements of a user interface of an insulin pump, a glucose meter or a remote control and initiate delivery of a predefined amount of insulin, determination of a glucose level, etc. Elements of such user interfaces include knobs, buttons, switches, sliders, display units, audio units, etc.

Medical devices must comply with very high standards as regards reliability, safety, etc., because incorrect operation of a medical device may have severe negative impacts to a patient's health. In some embodiments of medical devices, for example, in the event of administration of a bolus or another critical operation, the patient may be required to simultaneously press first and second user buttons for initiating delivery of the bolus or for performing the critical operation. The first and the second user buttons may be spaced sufficiently far away from each other, thereby preventing inadvertent or accidental delivery of the bolus or initiation of the critical operation. Thus, some embodiments of medical devices include a first control line which connects the first user button to a controller of the medical device and a second control line which connects the second user button to the controller of the medical device, wherein the controller is configured to detect if the first user button and the second user button are pressed simultaneously, and to initiate in this case a corresponding control operation such as the administration of a bolus or a critical operation.

WO 2009/013736 discloses a portable therapeutic fluid delivery device that includes a housing securable to the body of a patient, a reservoir coupled to the housing, a therapeutic fluid dispensing mechanism, and a bolus delivery button configured to signal a controller to initiate the delivery of the therapeutic fluid into the body of the patient. An inadvertent initiation prevention mechanism prevents the patient from activating the bolus delivery button. In an implementation, the therapeutic fluid delivery device comprises two or more bolus delivery buttons and the inadvertent initiation prevention mechanism prevents the controller from initiating the delivery of the therapeutic fluid into the body of the patient unless the patient activates the two or more delivery buttons substantially simultaneously or according to an activation sequence. In an implementation, electronic circuits of switches corresponding to the delivery buttons are connected to the ground on one end and to a power source as well as to a CPU's inlet port on the other end.

If a short circuit occurs in the control lines, in the electronic circuits, in the controller or in the CPU of a medical device, activation of only a single button may be wrongly detected as the simultaneous activation of a first and a second user button, thereby putting the medical device into a mode of operation which the user or patient did not intend, such as the delivery of a bolus or another critical mode of operation. Accordingly, compliance with very high standards as regards reliability, safety, etc., is degraded, which may have severe negative impacts to a patient's health.

SUMMARY

This disclosure provides a medical device for delivery of a medical fluid or for controlling delivery of a medical fluid as well as providing a method of operating such a medical device, which medical device and method do not have at least some of the disadvantages of the prior art. In particular, this disclosure teaches a medical device for delivery of a medical fluid or for controlling delivery of a medical fluid as well as providing a method of operating such a medical device, which enable generation of a short circuit alarm signal if a short circuit has occurred in the medical device. In particular, a medical device is taught for delivery of a medical fluid or for controlling delivery of a medical fluid as well as providing a method of operating such a medical device, wherein the medical device comprises a user interface associated with an electronic circuit connected to a first port and to a second port of a controller, wherein the electronic circuit enables the controller to detect actuation of the user interface, and wherein a short circuit alarm signal is generated if a short circuit has occurred.

According to this disclosure, a medical device is designed for delivering a medical fluid or designed for controlling delivery of a medical fluid, wherein the medical device comprises a user interface associated with an electronic circuit connected to a first port and to a second port of a controller, wherein the electronic circuit enables the controller to detect actuation of the user interface, wherein the controller is configured to execute the following sequence of steps: first step: to configure the first port as an output port and to apply a first signal to the first port; second step: to acquire a second signal from the second port; and third step: to determine on the basis of the second signal if a short circuit has occurred and to generate a short circuit alert signal if applicable. The controller includes first and second ports for detecting actuation of the user interface. In order to detect actuation of the user interface, the first and second ports are configured as input ports. In the sequence executed by the controller, one of the ports, in an embodiment the first port, is configured as an output port, thereby enabling a first signal to be applied to the first port. The first signal is transmitted to the electronic circuit. At the other of the ports, in the present embodiment at the second port, a second signal is acquired. The second signal depends on the electronic circuit. On the basis of the second signal, it is determined if a short circuit has occurred. The short circuit can have occurred in the electronic circuit, in the controller, etc. If it is determined that a short circuit has occurred, a short circuit alarm signal is generated. The short circuit alarm signal can be generated by changing the voltage of a corresponding signal line of the controller, by changing the value of a corresponding storage location in a memory of the controller, etc. The mode of operation of the medical device can be changed in accordance to the short circuit alarm signal, for example such that a critical mode of operation, for example the delivery of a bolus, is no longer possible.

In an embodiment, the electronic circuit is connected to a plurality of ports of the controller. In the first step one or more of the plurality of ports are configured as output ports and one or more first signals are applied to theses ports. In the second step, one or more second signals are acquired on one or more other ports, in particular one or more ports not being configured as output ports. In the third step, it is determined on the basis of one or more second signals if a short circuit has occurred and a short circuit alarm signal is generated if applicable.

In an embodiment, the controller is configured to detect prior to the first step if at least a part of the user interface is not actuated and to execute the sequence of steps only in case at least a part of the user interface is not actuated. If the user interface is actuated, the sequence of steps may result in the wrong detection of a short circuit.

In an embodiment, the controller is configured to detect prior to the first step if at least a part of the user interface is actuated and to wait for a predefined waiting time if at least a part of the user interface is actuated, and optionally to generate an alert signal after repeatedly waiting for a predefined waiting time and reaching a maximum total wait time. After the predefined waiting time, it can be tried to execute the sequence of steps. If a maximum waiting time has been reached, an alarm signal can be generated, which may be used to inform the user or patient that it cannot be currently detected if a short circuit has occurred, because of the user interface being currently actuated by the user or patient.

In an embodiment, the controller is configured following the third step to configure the first port as an input port. The first port is prepared for normal operation.

In an embodiment, the controller is configured that in the first step a ground voltage is applied to the first port, and that in the third step the short circuit alert signal is generated if the second signal does not equal a supply voltage.

In an embodiment, the controller is configured that the sequence of steps is executed at predefined times, at the end of predefined time intervals, at random times, at idle times of the medical fluid delivery device, at power on of the medical fluid delivery device, and/or on user request.

In an embodiment, the user interface includes a first user button and a second user button, wherein the controller is configured to initiate a predefined mode of operation of the medical device in case of a substantially simultaneous actuation of the first and second user button.

In an embodiment, the electronic circuit comprises a first line connecting the first port of the controller to a first pad and a second line connecting the second port of the controller to a second pad, wherein the first pad is connected via a first resistor to a supply voltage, wherein the first pad is connected via a first switch associated with the first user button to ground voltage, wherein the second pad is connected via a second resistor to the supply voltage, and wherein the second pad is connected via a second switch associated with the second user button to ground voltage.

In an embodiment, the medical device is an insulin pump, a glucose meter or a remote control.

Besides a medical device designed for delivering a medical fluid or designed for controlling delivery of a medical fluid, this disclosure concerns a method of operating a medical device designed for delivering a medical fluid or designed for controlling delivery of a medical fluid, wherein the medical device comprises a user interface associated with an electronic circuit connected to a first port and to a second port of a controller, wherein the electronic circuit enables the controller to detect actuation of the user interface, wherein the method includes the following sequence of steps: first step: configuring the first port as an output port and applying a first signal to the first port; second step: acquiring a second signal from the second port; and third step: determining on the basis of the second signal if a short circuit has occurred and generating a short circuit alert signal if applicable.

In an embodiment, the method includes detecting prior to the first step if at least a part of the user interface is not actuated and executing the sequence of steps only in case at least a part of the user interface is not actuated.

In an embodiment, the method includes detecting prior to the first step if at least a part of the user interface is actuated and waiting for a predefined waiting time if at least a part of the user interface is actuated, and optionally generating an alert signal after repeatedly waiting for a predefined waiting time and reaching a maximum total wait time.

In an embodiment, the method includes, following the third step, configuring the first port as an input port.

In an embodiment, the method includes in the first step applying a ground voltage to the first port, and in the third step generating the short circuit alert signal if the second signal does not equal a supply voltage.

In an embodiment, the method includes executing the sequence of steps according to at least one of the following: at predefined times, at the end of predefined time intervals, at random times, at idle times of the medical fluid delivery device, at power on of the medical fluid delivery device, and on user request.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

In the state of the art, medical devices for delivering a medical fluid or for controlling delivery of a medical fluid are widely used and include insulin pumps for delivering an amount of insulin, glucose meters for determining the glucose level, remote controls for controlling a medical device for delivering a medical fluid, etc.

Figure 1:
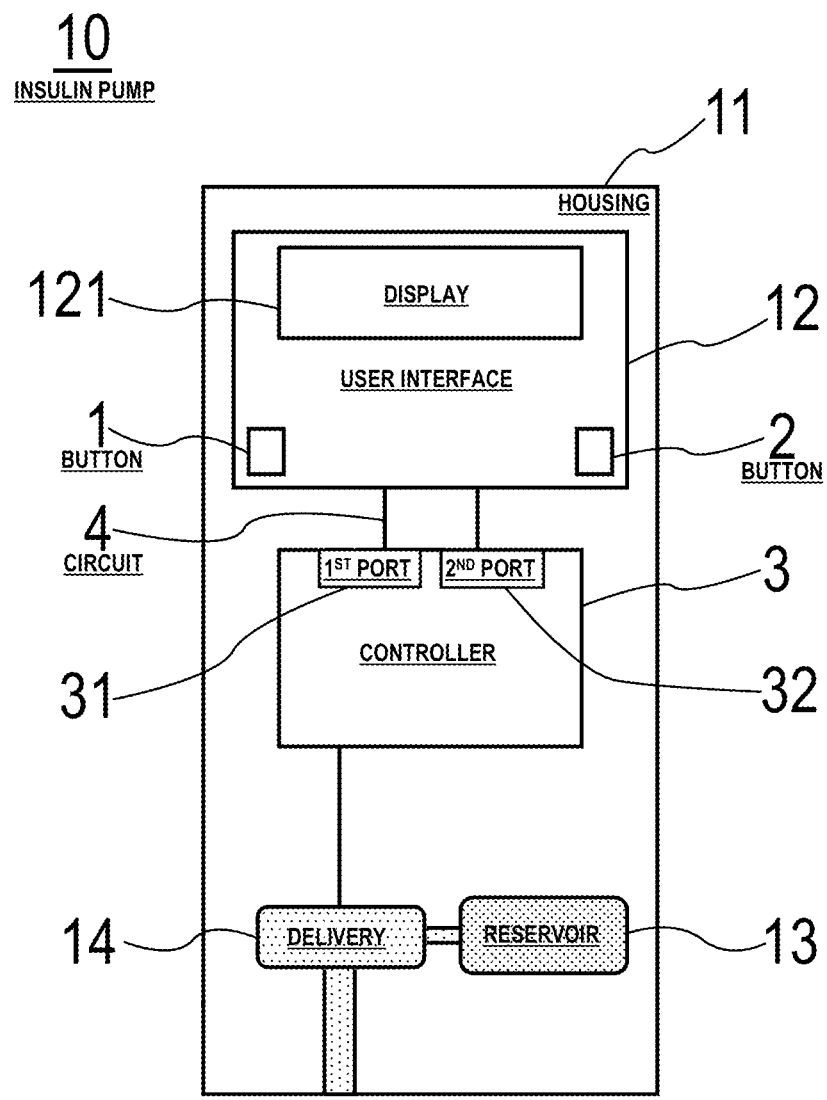
FIG. 1 illustrates schematically an insulin pump as an exemplary embodiment of a medical device.

As an illustrative example of such a medical device, FIG. 1 illustrates an insulin pump 10. However, the following disclosure may be equally well be applied to any medical device, such as a glucose meter for determining the glucose level, a remote control for controlling a medical device for delivering a medical fluid, etc.

The insulin pump 10 includes a housing 11 having a user interface 12, a controller 3 for controlling modes of operation of the insulin pump 10, a reservoir 13 for storing an amount of insulin, and a delivery mechanism 14 (e.g., a pump, drive, etc.) for delivering a predefined amount of insulin.

As illustrated in FIG. 1, the user interface 12 is associated with an electronic circuit 4. The electronic circuit 4 is connected to a first port 31 and to a second port 32 of the controller 3.

In an embodiment, the electronic circuit is connected to further ports of the controller 3 (not illustrated in FIG. 1).

As illustrated in FIG. 1, the user interface 12 includes a first user button 1 and a second user button 2. As will be described in more detail below, the controller 3 is enabled to detect via the electronic circuit 4 actuation of the user interface 12, such as actuation of the first user button 1 and/or actuation of the second user button 2.

The housing 11 includes materials such as for example plastic. In an embodiment, the housing 11 can have a modular design. For example, the housing 11 can include a first part and a second part. The first part of the housing 11 can have a reusable design having arranged for example the user interface 12, the electronic circuit 4, and the controller 3. The second part of the housing 11 can have a disposable design having arranged for example the reservoir 13 and the delivery mechanism 14. Other designs are possible.

The user interface 12 can include knobs, buttons, switches, sliders, display units, touchscreens, audio units, etc. As illustrated in FIG. 1, the user interface 12 includes a first user button 1 and a second user button 2. The first user button 1 and the second user button 2 may be arranged in such a manner, for example, at a sufficiently large distance from each other as indicated in FIG. 1, that inadvertent or accidental simultaneous actuation of the first user button 1 and the second user button 2 is not possible or highly unlikely.

As illustrated in FIG. 1, the user interface 12 may include a display unit (display) 121, for example for displaying status information such as units of a predefined amount of insulin, units of a bolus, etc.

The controller 3 can include a programmable microprocessor, logic circuits, digital to analogue converters, analogue to digital converters, amplifiers, etc.

The electronic circuit 4 can include electric lines, resistors, capacitors, inductors, connections to ground, connections to supply voltage, connections to supply current, etc.

The electronic circuit 4 is associated with the user interface 12. For example, the electronic circuit 4 is connected to switches which change states of connections in the electronic circuit 4 upon specific actuations of the user interface. For example, upon actuation of the first user button 1, a switch associated with the first user button 1 may close a specific connection between specific points in the electronic circuit, wherein after release of the first user button 1, the specific connection is interrupted.

The controller 3 includes a first port 31 connected to the electronic circuit 4 and a second port 32 connected to the electronic circuit 4. The connection of the electronic circuit 4 to the first and second port 31, 32 enables the controller 3 to detect actuations of the user interface, such as the actuation of the first user button 1 and the actuation of the second user button 2.

The controller 3 is configured to initiate a predefined mode of operation of the insulin pump 10 upon detection of a specific actuation of the user interface 12, such as a substantially simultaneous actuation of the first and the second user buttons 31, 32. The predefined mode of operation of the insulin pump 10 includes for example the delivery of a predefined amount of insulin, the delivery of a bolus, etc.

The reservoir 13 can have a reusable design, such that the reservoir 13 can be reused after depletion by refilling the reservoir. Alternatively, the reservoir 13 can have a disposable design, such that the reservoir is disposed after depletion.

The delivery mechanism 14 can include a pump mechanism for pumping an amount of insulin from the reservoir 13 via fluid lines connected to the reservoir 13 to a delivery tube designed for delivering a predefined amount of the medical fluid, i.e. the insulin.

For operation of the controller 3, the user interface 12, the delivery mechanism 14, etc., the insulin pump 10 includes an energy source such as a battery, a rechargeable battery, etc.

Figure 2:
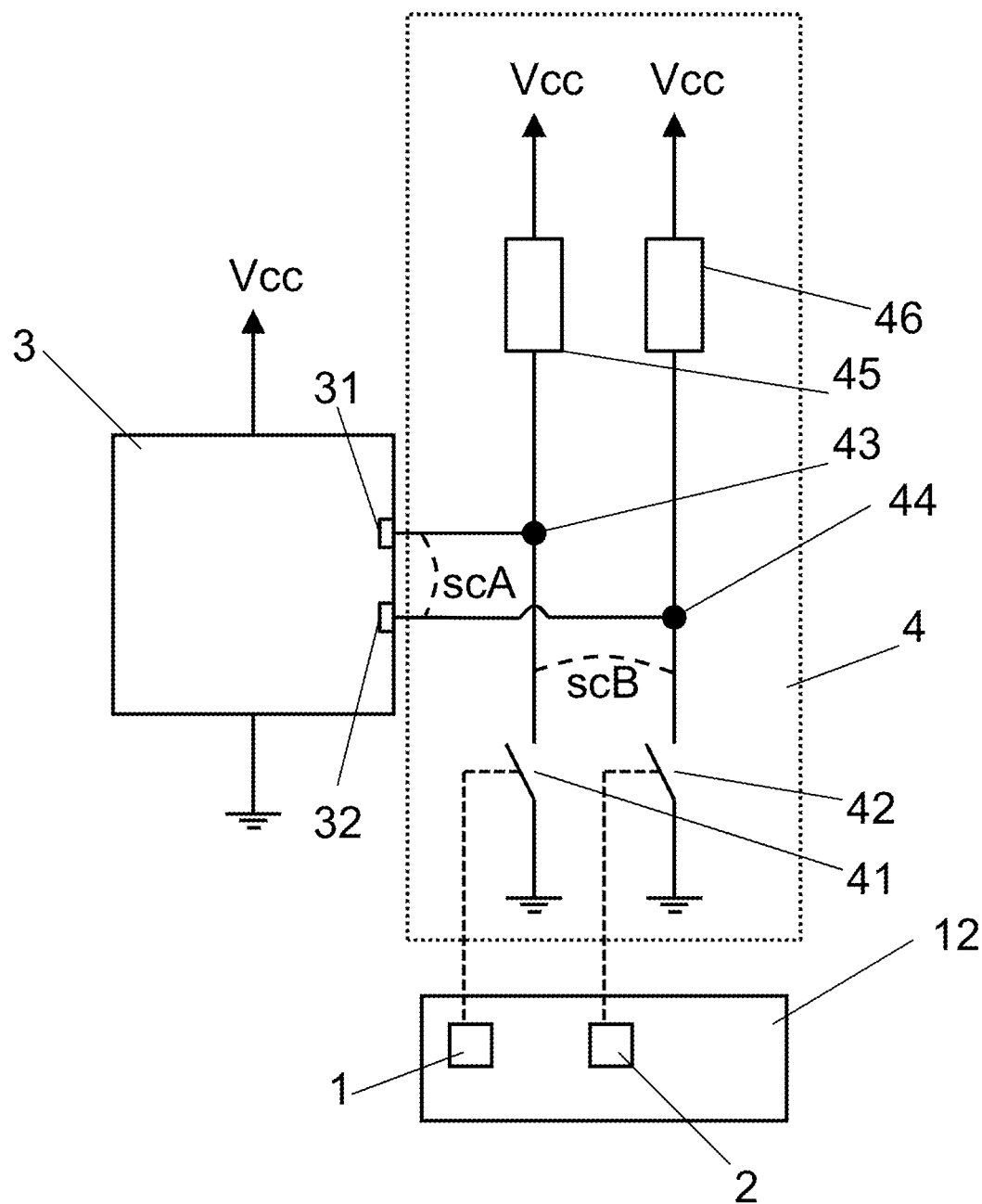
FIG. 2 illustrates schematically a user interface associated with an electronic circuit connected to a controller for determining if a first user button and a second user button of the user interface have been actuated substantially simultaneously.

FIG. 2 illustrates schematically in more detail the controller 3, the electronic circuit 4 and the user interface 12 of the insulin pump 10, which enabled determining if a first user button 1 and a second user button 2 of the user interface 12 have been actuated substantially simultaneously.

As illustrated in FIG. 2, for delivering operational energy to the controller 3, the controller 3 is connected to supply voltage Vcc and to ground voltage. The controller 3 includes a first port 31 and a second port 32.

The user interface 12 includes a first user button 1 and a second user button 2, which can be actuated by a user.

The user interface 12 is associated with the electronic circuit 4, which is illustrated in FIG. 2 with dotted lines. In particular, the first user button 1 of the user interface 12 is designed to actuate a first switch 41 of the electronic circuit 4, which is illustrated in FIG. 2 with dashed lines. The second user button 2 of the user interface 12 is designed to actuate a second switch 42 of the electronic circuit 4, which is illustrated in FIG. 2 with dashed lines.

In an embodiment, the first user button 1 and/or the first switch 41 and the second user button 2 and/or the second switch 42 include a spring mechanism, which provides that when a user or patient actuates the first user button 1 or second user button 2, for example, by pressing the first user button, that the first switch 41 or the second switch 42 is closed, thereby closing a connection between one end of the switch and another end of the switch, and that as soon as the user or patient no longer actuates the first user button 1 or second user button 2, for example, by releasing the first user button 1 or second user button 2, the first switch 41 or the second switch 42 is opened, thereby interrupting a connection between the one end of the switch and the other end of the switch.

By actuating the first user button 1, a user or patient can switch the first switch 41 from an open position (as illustrated in FIG. 2) to a closed position (not illustrated in FIG. 2). By actuating the second user button 2, a user or patient can switch the second switch 42 from an open position (as illustrated in FIG. 2) to a closed position (not illustrated in FIG. 2).

One end of the first switch 41 is connected to ground voltage. The other end of the first switch 41 is connected to a first pad 43, which is further connected to the first port 31 and via a resistor 45 to supply voltage Vcc. One end of the second switch 42 is connected to ground voltage. The other end of the second switch 42 is connected to a second pad 44, which is further connected to the second port 32 and via a resistor 46 to supply voltage Vcc.

By actuating the first user button 1 or the second user button 2, a user or patient can switch the first pad 43 or the second pad 44 between supply voltage Vcc and ground voltage. The controller 3 can sense the voltage level of the first pad 43 or the second pad 44 and thereby determine if a user or patient actuates the first user button 1 or the second user button 2.

In particular, by sensing the voltage level of the first pad 43 and the second pad 44, the controller 3 can sense if the user or patient actuates the first user button 1 and the second user button 2 substantially simultaneously.

In the open position of the first switch 41 or the second switch 42 illustrated in FIG. 2, the voltage level of the first pad 43 or the second pad 44 is at supply voltage Vcc.

As illustrated in FIG. 2, at various locations of the control circuit 4, short circuits scA, scB can occur. As illustrated in FIG. 2, the short circuit with reference sign scA may occur between the line connecting the first port 31 with the first pad 43 and the line connecting the second port 32 with the second pad 44. As illustrated in FIG. 2, the short circuit with reference sign scB may occur between the line connecting the first switch 41 with the first pad 43 and the line connecting the second switch 42 with the second pad 42. Moreover (not illustrated in FIG. 2), a short circuit may occur between the first pad 43 and the second pad 44. Moreover (not illustrated in FIG. 2), a short circuit may occur between the line connecting the first pad 43 with the first resistor 45 and the line connecting the second pad 44 with the second resistor 46. Moreover (not illustrated in FIG. 2), a short circuit may occur internally in the controller 3, for example between the first port 31 and the second port 32.

A short circuit has the effect that the voltage level of the first pad 43 and the voltage level of the second pad 44 have the same value.

Thus, in case of a short circuit, if the user or patient actuates simply the first user button 1 alone, both the first pad 43 and the second pad 44 change the voltage level from supply voltage Vcc to ground voltage. Accordingly, the controller 3 wrongly detects that a user or patient has actuated both the first user button 1 and the second user button 2 simultaneously, thereby potentially initiating a mode of operation which may not be adapted (or even dangerous) for the user or patient.

Figure 3:
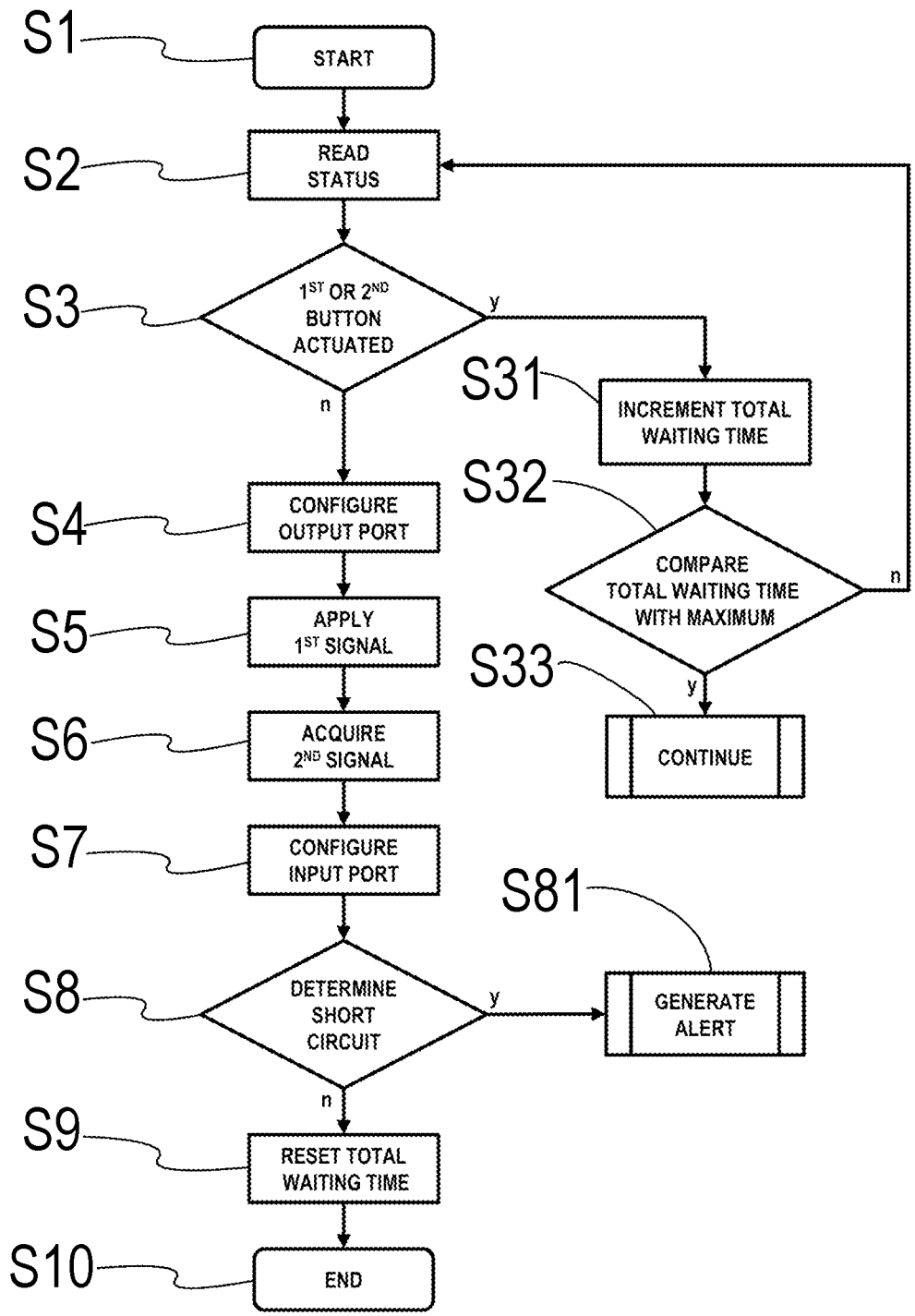
FIG. 3 illustrates schematically a sequence of steps for determining if a short circuit has occurred.

FIG. 3 illustrates schematically a sequence of steps performed by the controller 3 connected to the electronic circuit 4 associated with the first user button 1 and the second user button 2 in order to determine if a short circuit has occurred.

In the following, the sequence of steps is illustrated for the lines of the first user button 1. However, by applying steps S4, S5, S6, S7, and S8 to the lines of the second user button 2 instead of the first user button 1, the sequence of steps can be performed equally well for the lines of the second user button 2.

In step S1, the sequence of steps for determining if a short circuit has occurred starts.

In step S2, the controller 3 reads the status of the first user button 1 and the second user button 2, namely by determining the voltage level of the first pad 43 and the second pad 44, wherein if the voltage level of the first pad 43 and the second pad 44 is determined to equal supply voltage Vcc, it is determined that neither the first user button 1 nor the second user button 2 is actuated by a user or patient. If the voltage level of the first pad 43 is determined to equal ground voltage, it is determined that the first user button 1 is actuated by a user or patient. If the voltage level of the second pad 44 is determined to equal ground voltage, it is determined that the second user button 2 is actuated by a user or patient.

In step S3, it is determined if the status indicates if either the first user button 1 or the second user button 2 is actuated by a user or patient. If yes, the sequence of steps is continued with step S31. If no, the sequence of steps is continued with step S4.

In step S31, the value of a total waiting time, which is stored for example in a memory location of controller 3, is incremented by a predetermined value, for example by one second.

In step S32, the value of the total waiting time is compared with a predefined maximum waiting time. If the total waiting time equals or exceeds the maximum waiting time, the sequence of steps is continued with step S33, which may include an optional alarm, as described above. If the total waiting time is below the maximum waiting time, the sequence of steps is continued with step S2.

In step S4, the first port 31 of the controller 3 is configured as an output port (if the sequence of steps is performed for the lines of the second user button 2 instead of the first user button 1, the second port 32 instead of the first port 31 is configured as an output port). As the controller 3 is configured in normal operation to determine whether the user or patient actuates the first user button or the second user button, the first port 31 and the second port 32 are normally configured as input ports. However, in step S4, the first port 31 (or the second port 32) is configured as an output port.

In step S5, a first signal is applied to the first port 31. In a variant, the first signal is a voltage having a constant level. In a variant, the first signal is the ground voltage.

In step S6, a second signal is acquired from the second port 32. In a variant, the second signal is acquired during a predetermined time interval.

In step S7, the first port 31 of the controller 3 is configured as an input port, thereby preparing and enabling normal operation of the controller 3.

In step S8, it is determined on the basis of the second signal if a short circuit has occurred. In a variant, in case of a first signal having a constant level and if the second signal has the same level as the first signal, it is determined that a short circuit has occurred. In a variant, in case of a first signal having ground voltage and if the second signal is ground voltage, it is determined that a short circuit has occurred. In a variant, if the second signal is not supply voltage, it is determined that a short circuit has occurred. If it is determined that a short circuit has occurred, the sequence of steps continues with step S81. If it is not determined that a short circuit has occurred, the sequence of steps continues with step S9.

In step S81, a short circuit alert signal is generated. In a variant, the short circuit alert signal is applied to a signal line of the controller 3. In a variant, the short circuit alert signal is indicated by setting a predefined storage location in the memory of the controller 3 to a predefined value.

In step S9, the total waiting time according to step S31 is reset, thereby preparing a next run of the sequence of steps for determining if a short circuit has occurred.

In step S10, the sequence of steps for determining if a short circuit has occurred ends.

The sequence of steps for determining if a short circuit has occurred can be executed for the lines of the first user button 1 or for the lines of the second user button 2.

The sequence of steps for determining if a short circuit has occurred can be executed for the lines of the first user button 1 and directly following for the lines of the second user button 2.

The sequence of steps for determining if a short circuit has occurred can be executed alternately for the lines for the first user button 1 and for the lines of the second user button 2.

The sequence of steps for determining if a short circuit has occurred can be executed upon powering on the medical device 10.

The sequence of steps for determining if a short circuit has occurred can be executed periodically, for example at each full hour.

In case the user or patient is using the medical device, the sequence of steps for determining if a short circuit has occurred can be postponed by a predetermined amount of time. If the sequence of steps for determining if a short circuit has occurred cannot be executed after the predetermined amount of time, an alarm signal can be generated.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A medical device for delivering a medical fluid, comprising:
   a user interface;
   an electronic circuit connecting the user interface to first and second ports of a controller, wherein the electronic circuit enables the controller to detect actuation of the user interface, further wherein the controller is configured to perform the following steps:
   use the first port as an output port and to apply a first signal to the first port;
   cause the first signal to be transmitted to the electronic circuit;
   acquire a second signal from the second port, the second signal depending on the status of the circuit; and
   to determine from the second signal when a short circuit has occurred and to generate a short circuit alert signal;
   wherein the controller is further configured to use the first port as an input port following the acquiring of the second signal from the second port.

2. The medical device according to claim 1, wherein the controller is configured to detect when at least a part of the user interface is not actuated.

3. The medical device according to claim 1, wherein the controller is configured to detect when at least a part of the user interface is actuated and to wait for a predefined waiting time when at least a part of the user interface is actuated.

4. The medical device according to claim 1, wherein the controller is further configured to use the first port as an input port following the determination from the second signal that a short circuit has occurred.

5. The medical device according to claim 1, wherein the controller is configured to apply a ground voltage to the first port and to generate the short circuit alert signal when the second signal does not equal a supply voltage.

6. The medical device according to claim 1, wherein the controller is configured that the steps according to claim 1 are executed according to at least one of the following: at predefined times, at the end of predefined time intervals, at random times, at idle times of the medical fluid delivery device, at power on of the medical fluid delivery device, and on user request.

7. The medical device according to claim 1, wherein the user interface includes first and second user buttons and the controller is configured to initiate a predefined mode of operation of the medical device in response to a substantially simultaneous actuation of the first and second user buttons.

8. The medical device according to claim 1, wherein:
   the user interface includes first and second user buttons;
   the electronic circuit comprises a first line connecting the first port to a first pad and a second line connecting the second port to a second pad;
   the first pad is connected via a first resistor to a supply voltage and is connected via a first switch associated with the first user button to ground voltage; and
   the second pad is connected via a second resistor to the supply voltage and is connected via a second switch associated with the second user button to ground voltage.

9. The medical device according to claim 1, comprising at least one of an insulin pump, a glucose meter and a remote control.

10. A method of delivering a medical fluid using a device having a user interface and an electronic circuit connecting the user interface to first and second ports of a controller, the electronic circuit enabling the controller to detect actuation of the user interface, the method comprising:
    (a) using the first port as an output port and applying a first signal to the first port;
    (b) causing the first signal to be transmitted to the electronic circuit;
    (c) acquiring a second signal from the second port, the second signal depending on the status of the circuit;
    (d) determining from the second signal when a short circuit has occurred and generating a short circuit alert signal; and
    (e) after step (c) or step (d), configuring the first port as an input port.

11. The method according to claim 10, further comprising, prior to step (a), detecting that at least a part of the user interface is not actuated.

12. The method according to claim 10, further comprising, prior to step (a), detecting when at least a part of the user interface is actuated and waiting for a predefined waiting time.

13. The method according to claim 10, further comprising, after step (d), configuring the first port as an input port.

14. The method according to claim 10, further comprising applying a ground voltage to the first port in step (a) and generating the short circuit alert signal in step (d) in response to the second signal not equaling a supply voltage.

15. The method according to claim 10, wherein steps (a)-(e) are executed according to at least one of the following: at predefined times, at the end of predefined time intervals, at random times, at idle times of the medical fluid delivery device, at power on of the medical fluid delivery device, and on user request.

\* \* \* \* \*